United States Patent [19]

Avidan et al.

[11] Patent Number: 4,513,160

[45] Date of Patent: Apr. 23, 1985

[54] PROCESS FOR THE CONVERSION OF ALCOHOLS AND OXYGENATES TO HYDROCARBONS IN A TURBULENT FLUID BED REACTOR

[75] Inventors: Amos A. Avidan, Mantua; Anthony Y. Kam, Cherry Hill, both of N.J.

[73] Assignee: Mobil Oil Corporation, New York, N.Y.

[21] Appl. No.: 479,521

[22] Filed: Mar. 28, 1983

[51] Int. Cl.$^3$ ............................ C07C 1/00; C07C 1/20
[52] U.S. Cl. .................................... 585/640; 208/158; 422/139
[58] Field of Search ................ 208/158, 159; 585/639, 585/640; 422/139, 143, 146

[56] References Cited

U.S. PATENT DOCUMENTS

| | | | |
|---|---|---|---|
| 2,468,508 | 4/1949 | Munday | 422/143 |
| 2,719,112 | 9/1955 | Kearby et al. | 208/158 |
| 3,169,835 | 2/1965 | Huntley et al. | 208/158 |
| 4,025,576 | 5/1977 | Chang et al. | |
| 4,052,479 | 10/1977 | Chang et al. | |
| 4,071,574 | 1/1978 | Milstein et al. | 585/640 |
| 4,134,926 | 1/1979 | Tsao et al. | 585/640 |
| 4,197,418 | 4/1980 | Lee et al. | |
| 4,229,608 | 10/1980 | Chen et al. | |
| 4,238,631 | 12/1980 | Daviduk et al. | |
| 4,328,384 | 5/1982 | Daviduk et al. | |
| 4,338,475 | 7/1982 | Pennington et al. | |
| 4,409,416 | 10/1983 | Snell et al. | 585/639 |
| 4,469,050 | 9/1984 | Korenberg | 110/245 |

FOREIGN PATENT DOCUMENTS 0099690  1/1984  European Pat. Off. .

OTHER PUBLICATIONS

Kehoe & Davidson, "Continuously Slugging Fluidized Beds", 1971.
Powder Technology, vol. 24, No. 2, 1979, Lausanne J. Yerushalmi and N. T. Cankurt, "Further Studies of the Regimes of Fluidization", pp. 187–205, p. 193, left-hand col., lines 10–21.
Ullmanns, "Encyklopadie der technischem Chemie", 4th Edition, vol. 1, Allgemeine Grundlagen der Verfahrens-und Reaktions-technik, 1972; Verlag Chemie GmbH, Weinhem, pp. 237–239, p. 237, right-hand col., line 19; p. 238, left-hand col., line 56.

Primary Examiner—Delbert E. Gantz
Assistant Examiner—Anthony McFarlane
Attorney, Agent, or Firm—A. J. McKillop; M. G. Gilman; L. G. Wise

[57] ABSTRACT

Improvements in converting $C_1$–$C_3$ monohydric alcohols, particularly methanol, related oxygenates of said alcohols and/or oxygenates produced by Fischer-Tropsch synthesis to light olefins, gasoline boiling range hydrocarbons and/or distillate boiling range hydrocarbons are obtained in a fluidized bed of ZSM-5 type zeolite catalyst operating under conditions effective to provide fluidization in the turbulent regime.

3 Claims, No Drawings

PROCESS FOR THE CONVERSION OF ALCOHOLS AND OXYGENATES TO HYDROCARBONS IN A TURBULENT FLUID BED REACTOR

BACKGROUND OF THE INVENTION

1. Field of the Invention

This invention relates to the production of light olefins, hydrocarbons boiling in the gasoline boiling range or the distillate boiling range and mixtures thereof from lower aliphatic alcohols, related and other oxygenates, and mixtures thereof. More particularly, it relates to the catalytic conversion of an alcohol or oxygenate-containing feed to olefins and/or $C_5+$ hydrocarbons. This invention especially relates to the conversion of $C_1-C_3$ monohydric alcohols, related oxygenates and/or Fisher-Tropsch oxygenates to light olefins, gasoline boiling range hydrocarbons and/or distillate boiling range hydrocarbons in a bed of ZSM-5 type zeolite catalyst operating in the turbulent fluidization regime.

2. Description of the Prior Art

The growing demand for fuels and light petroleum products, including light olefin gases, and the growing shortage of crude oil supply, has resulted in a continuing strong interest in tapping alternate raw material sources from which to obtain the desired light hydrocarbon products.

In recent years, the patent art has disclosed that alcohols and related oxygenates, which may be obtained from coal, natural gas or biomass, can be converted to more complex hydrocarbons, including gasoline boiling hydrocarbons, by utilizing a novel group of zeolites, exemplified by ZSM-5 zeolite. In one commercial aspect the process is employed as part of the conversion of natural gas to gasoline. Here natural gas is steam reformed to synthesis gas which in turn is converted to methanol. The methanol is then converted to gasoline employing Mobil Oil Corporation's MTG (methanol to gasoline) process. The MTG process is disclosed in the patent art, including, for example, U.S. Pat. Nos. 3,894,103; 3,894,104; 3,894,107; 4,035,430 and 4,058,576. U.S. Pat. No. 3,894,102 discloses the conversion of synthesis gas to gasoline.

The conversion of lower monohydric alcohols to gasoline by the catalytic action of ZSM-5 type zeolites is highly exothermic. To control this exothermic heat, a number of patentees have employed fluidized catalyst techniques which were developed heretofore, principally in the petroleum industry. Fluidization methods have been usefully employed in the cracking of gas oils where the powdered catalyst was used to transfer heat, developed during the regeneration of the catalyst in a fluidized bed, to another fluidized bed of catalyst to effect the endothermic cracking of the gas oil.

A number of commonly assigned patents and patent applications disclose the use of fluidized bed techniques not only to control the heat released in the conversion of alcohols to gasoline but also, because of the intimate contact between reactants and catalyst provided by the fluidized catalyst, to improve product selectivity and catalyst life. However, the nature of the fluidized catalyst bed employed promotes the growth of bubbles of reactant gases and the backmixing of the gasiform materials, both of which are undesirable. These prior art patents have addressed these problems in a variety of ways. Thus, U.S. Pat. No. 4,071,573 of Owen et al. discloses the use of horizontally disposed grid means, such as wire mesh screens or heat exchanger means, in a dilute phase catalyst riser reactor to disperse reactant or product gas bubbles as the catalyst-reactant suspension passes upwardly through the riser. A plurality of vertical baffles is provided in the dense phase fluid catalyst bed disclosed in U.S. Pat. No. 4,197,418 of Lee et al. which are said to restrict upflowing reactant bubble growth so as not to exceed about six inches and to provide substantial plug flow conditions. U.S. Pat. Nos. 4,238,631 and 4,251,484 of Daviduk et al. disclose a dense fluidized bed reactor for methanol conversion provided with a plurality of vertical heat exchanger tubes and vertical open end baffle tubes which are spaced to provide a flow path having a hydraulic diameter of four to eight inches when the reactants are in contact with the fluid mass of catalyst particles. Commonly assigned patent application Ser. No. 400,203, filed July 20, 1982 discloses the use of a dense fluidized bed reactor provided with a plurality of horizontally disposed baffles which result in a increase in the conversion efficiency as compared to a unbaffled or vertically baffled dense fluidized bed reactor. The entire contents of these four commonly assigned patents are incorporated herein by reference.

These prior art patents are concerned with various types of horizontal and vertical baffles for dispersing gas bubbles in the fluidized bed. Specifically, Lee et al. is concerned with breaking up bubbles to not more than six inches, preferably not more than four inches while Daviduk et al's U.S. Pat. No. 4,251,484 speaks of restricting gas bubble growth to less than twenty-four inches, preferably not to exceed eight inches. The baffles in the reactor of Daviduk et al. provide a hydraulic diameter of the vertical passageways of four to eight inches.

It is an object of the invention to improve the prior art processes which employ dense fluid bed technology for the conversion of lower alcohols and oxygenates to light olefins, gasoline boiling hydrocarbons and/or distillate boiling range hydrocarbons.

It is another object of this invention to provide a process for the conversion of lower alcohols and oxygenates to light olefins, gasoline boiling range hydrocarbons and/or distillate boiling range hydrocarbons by means of a fluidized ZSM-5 type zeolite catalyst.

It is a further object of this invention to provide a process for the conversion of lower alcohols and oxygenates to light olefins, gasoline and/or distillate fuels by means of a ZSM-5 type zeolite catalyst in a fluidized system which provide the gaseous reaction mixture in a series of bubbles which are small, random and short-lived thereby providing good contact between the gaseous reactants and the catalyst particules.

The achievement of these and other objects will be apparent from the following description of the subject invention.

SUMMARY OF THE INVENTION

In accordance with the present invention, it has been found that significant improvements can be made in the process of converting a $C_1-C_3$ aliphatic alcohol, particularly methanol, related oxygenates of said alcohol, and/or oxygenates from Fischer-Tropsch synthesis to light olefins, gasoline boiling range hydrocarbons and/or distillate boiling range hydrocarbons with a ZSM-5 type catalyst in a fluidized bed reactor by operating in the turbulent fluidization regime.

In particular, this invention relates to an improvement in a process for converting reactants comprising $C_1$-$C_3$ monohydric alcohols, related oxygenates thereof and/or oxygenates produced by Fischer-Tropsch synthesis at a conversion of at least 70% to a hydrocarbon product higher boiling than the reactants and comprising light olefins, gasoline-boiling range hydrocarbons and/or distillate boiling range hydrocarbons wherein a reactant comprising a $C_1$—$C_3$ monohydric alcohol, a related oxygenate and/or an oxygenate produced by Fischer-Tropsch synthesis alone or in admixture with water is passed through a fluidized bed of catalyst particles comprising ZSM-5 type crystalline zeolite, said improvement comprising: passing the reactant through a fluidized bed under conditions effective to provide fluidization in the turbulent regime.

DESCRIPTION OF THE PREFERRED EMBODIMENTS

The process of the present invention relates to a catalytic process of converting a lower monohydric alcohol, an oxygenate thereof and a Fisher-Tropsch oxygenate to light olefins, gasoline boiling range hydrocarbons and/or distillate boiling range hydrocarbons in a fluidized bed of ZSM-5 type crystallin zeolite operating under conditions effective to provide fluidization in the turbulent regime. In a preferred embodiment the alcohol is methanol.

The feed to the process of this invention may include a $C_1$-$C_3$ monohydric alcohol alone or a mixture of said alcohols. The feed may also include admixtures of said alcohol, or alcohols, related oxygenates and/or oxygenates produced by Fischer-Tropsch synthesis alone, admixtures thereof or in admixture with water. Examples of related oxygenates are the ethers of the useful alcohols, i.e., dimethyl ether is a related oxygenate of methanol. Water may comprise 0 to about 20 weight percent of the feed to this process where conversions of at least 95% are desired. Where partial conversions of at least 40%, preferably at least about 70%, are desired water may comprise up to about 60% weight percent of the feed.

The $C_1$–$C_3$ monohydric alcohols that may be charged to the process of this invention, include methanol, ethanol, propanol, and isopropanol. The feed may consist of a relatively pure single alcohol, or mixtures of these alcohols. In general, any mixture comprising methanol, ethanol, propanol, isopropanol or mixtures thereof and which is convertible with high exothermicity, is a suitable feed for the present invention. Conversions which produce more than about 100 BTU/lb of total hydrocarbon product, and preferably more than about 200 BTU/lb of hydrocarbon product, at conversion temperature, are considered highly exothermic for the purpose of the present invention.

The preferred charge of the present invention and the one utilized in the detailed descriptions of the invention is methanol together with 0 to about 20 weight percent water. Mixtures of methanol and dimethyl ether are also included as preferred charges.

In the following description, the process of the invention will be described with methanol serving as the feedstream. This has been done for convenience and for illustrative purposes only since it will be appreciated that the feed can comprise any of the other alcohols, or oxygenates described herein either alone or admixed with water.

The conversion effected in the present invention is conducted in the presence of crystalline zeolite catalysts which are members of a novel class of zeolites known in the art as ZSM-5 type zeolites.

In general, the ZSM-5 type zeolite catalysts used in accordance with this invention are crystalline zeolites having a silica/alumina ratio greater than 12 and a Constraint Index (C.I.) between about 1 and about 12. These zeolites and their use as conversion catalysts for lower aliphatic alcohols are described in the prior art, particularly U.S. Pat. Nos. 3,894,106, 4,025,571, 4,058,576 and 4,148,835. The entire contents of these patents are incorporated herein by reference.

The preferred class of zeolites described above are ZSM-5 type zeolites as exemplified by ZSM-5, ZSM-11, ZSM-12, ZSM-23, ZSM-35 and ZSM-38, with ZSM-5 being particularly preferred.

ZSM-5 is more particularly described in U.S. Pat. No. 3,702,886, the entire contents of which are incorporated herein by reference.

ZSM-11 is more particularly described in U.S. Pat. No. 3,709,979, the entire contents of which are incorporated herein by reference.

ZSM-12 is more particularly described in U.S. Pat. No. 3,832,449, the entire contents of which are incorporated herein by reference.

ZSM-23 is more particularly described in U.S. Pat. No. 4,076,842, the entire contents of which are incorporated herein by reference.

ZSM-35 is more particularly described in U.S. Pat. No. 4,016,245, the entire contents of which are incorporated herein by reference.

ZSM-38 is more particularly described in U.S. Pat. No. 4,046,859, the entire contents of which are incorporated herein by reference.

Particularly preferred catalysts within the above descriptions are ZSM-5 type zeolite catalysts made with large crystal ZSM-5, i.e. a crystal size of at least 1 micron, as described in U.S. Pat. Nos. 4,025,571 and 4,148,835, the entire contents of which are incorporated herein by reference.

The present invention is concerned with improving the conversion of alcohols to higher boiling hydrocarbons, particularly methanol to gasoline boiling hydrocarbons. In particular the present invention concerns the operation of a fluidized bed of ZSM-5 type catalyst in the so called turbulent fluidization regime by proper choice of catalyst physical properties, reactor configuration, and superficial fluid velocity in the reactor bed. By virtue of the turbulence experienced in this regime, gas-solid contact in the catalytic reactor is improved, insuring proper conversion and selectivity. One main feature of this concept is the inherent control of bubble size and characteristic bubble lifetime. Bubbles of the gaseous reaction mixture are small, random and short-lived, thus resulting in good contact between the gaseous reactants and the solid catalyst particles.

The main difference between the process of this invention and the alcohol and oxygenate conversion processes discussed hereinabove is that operation in the turbulent fluidization regime is employed herein. The main advantage of operation in such a mode is the control of bubble size and life span, thus avoiding large scale gas by-passing in the reactor. The process of the present invention does not rely on internal baffles in the reactor for the purpose of bubble size control such as the baffles which are employed in the prior art processes discussed above.

Fluidization is a gas-solid contacting process in which a bed of finely divided solid particles is lifted and agitated by a rising stream of gas. Fluidization occurs in a bed of particulates when an upward flow of fluid through the interstices of the bed of particles attains a frictional resistance equal to the weight of the bed. At this point, an incremental increase in the fluid rate lifts or supports the particles. This condition is referred to as incipient buoyancy, since at this fluid rate, the particles are still so close as to have essentially no mobility. Where it is desired to create bed homogeneity, the fluid velocity can be increased to the point of blowing bubbles or voids into the bed which is then violently mixed as the bubbles rise. The increased fluid velocity at which bubbles first form is called the incipient-bubbling velocity.

In the past research workers tested a wide variety of materials to study the fluidization effects thereon. However, the conclusions drawn from data on the fluidization of one particulate matter were found not to be applicable to other powders which had quite different particle sizes and densities. Geldart (7 *Powder Technology* 285 (1973)) reports that the behavior of solids fluidized by gases falls into four clearly recognizable groups, characterized by the difference in density between the particular particles and the fluidizing fluid and the mean size of the particles. Powders in group A exhibit a dense phase expansion after minimum fluidization and prior to the commencement of bubbling, group B powders bubble at the minimum fluidization velocity; the powders in group C are difficult to fluidize at all and those in group D can form stable spouted beds. The group A and B powders are those of most importance in fluidization. Fluid catalytic cracking catalyst is a typical group A powder while sand is the most typical group B powder.

The group A materials have a small mean size and/or a low particle density (usually less than about 1.4 g/cm$^3$). Group A powders expand considerably before bubbling commences. When the gas supply is suddenly cut off the bed collapses slowly. Gross circulation of a group A powder occurs even when few bubbles are present, producing rapid mixing. Bubbles in a two-dimensional bed appeared to split and recoalesce very frequently. All bubbles rise more rapidly than the interstitial gas velocity, but in freely bubbling beds the velocity of small bubbles (less than 4 cm) appears to be about 30–40 cm/s regardless of bubble size. As the superficial gas velocity is increased in a group A powder bed, eventually slugging conditions occur and with a further increase in the superficial gas velocity the slug flow breaks down into a turbulent regime. The velocity at which this turbulent regime occurs appears to decrease with particle size.

The group B powders are of less importance in fluidization. They consist of materials in the particle size of 40 to 500 $\mu$m and a density of 1.4–4 g/cm$^3$. With Group B powders bubbling starts to form at or only slightly above the minimum fluidization velocity. Bed expansion is small and the bed collapses very rapidly when the gas supply is cut off. There is little or no circulation of the group B powder in the absence of bubbles. Most bubbles rise more quickly than the interstital gas velocity. Gas velocity can be increased until slugging commences however, there is conflicting evidence regarding the breakdown of slugging into turbulent flow which takes place with group A powders.

The most easily observed difference between the group A and group B powders is whether or not the bed bubbles at or near the minimum fluidization point. If there is an appreciable bed expansion before bubbling commences, than the powder belongs to group A. The group A powders can than be defined as those in which the ratio of the superficial gas velocity at minimum bubbling conditions to the superficial gas velocity at minimum fluidization is greater than one.

The turbulent regime results from increasing the gas velocity in a heterogenous, bubbling fluidized bed. The two-phase character of the bubbling bed first peaks, then gradually changes giving way to a condition of increasing uniformity culminating in the turbulent state in which large discrete bubbles or voids are on the whole absent. A bubbling fluidized bed consists of large bubbles or slugs of gas which pass upwardly through the bed of particles causing a heterogenous mixture of gas and solid particles. Like a bubbling fluidized bed, a turbulent fluidized bed has an upper bed surface though it is considerably more diffuse than in a bubbling fluidized bed because of the greater freeboard activity attending the operation at higher gas velocities. The turbulent regime extends from the transition velocity to the so-called transport velocity. (Yerushalmi et al., *Further Studies of the Regimes of Fluidization*, 24 Powder Tech. 187–205 (1979).) As the transport velocity is approached, there is a sharp increase in the rate of particle carryover, and in the absence of solid recycle, the bed would empty in short order.

The transition from bubbling fluidized bed to the turbulent regime of fluidization is gradual and spans a range of gas velocities which depend on the properties of gas and solids and on equipment scale as well. The transition may be bracketed and thus characterized by two velocities: the velocity at which the pressure fluctuations peak and the velocity at which the fluctuations naving decayed from their peak value, begin to level off. This velocity at the leveling off point marks the end of the transition and the onset of the turbulent regime. Although no exact correlations exist, in general both the velocity at the peaking of pressure fluctuations and the velocity at the leveling off of the fluctuations increase with both particle size and density. (Yerushalmi et al., supra.)

The transition from bubbling to turbulent fluidization involves a gradual breakdown of large bubbles into small bubbles and voids. The process of bubble splitting is to some extent counterbalanced by coalescence of the resulting smaller bubbles, but the net effect is a progressive change toward a structure of greater homogeneity, culminating in the turbulent state where, on the whole, large discrete bubbles are absent. The change that takes place as the velocity of the gas spans the transition from bubbling to turbulent fluidization may be described as a process of dispersion. Large bubbles and slugs split, dispersing as smaller voids in the mass of solids. Simultaneously, the dense phase expands, but the expansion is not uniform. Instead, the solid too disperses, divided by the action of the lean phase into clusters and streamers. As a result, the structure of a turbulent fluid bed is more homogeneous consisting of two phases, of which neither can be viewed as either continuous or discontinuous.

The steady process of coalescence and splitting of the lean phase voids sets into motion a similar phenomenon in the dense phase. Together these lend the regime its "turbulent" character. Solid mixing is vigorous, the interaction of the two phases is strong, and the contact between gas and solid is highly efficient. For a fluid catalytic cracking catalyst having a transfer velocity around 1.2–1.5 m/sec., the turbulent regime stretches from about 0.6 m/sec. to a velocity around 1.2–1.5 m/sec. Over this range, the fluidized density measured at the bottom of the bed remains rather high-ranging from about 200 to about 335 kg/m$^3$.

Since the fluidized bed of ZSM-5 zeolite catalyst of the present invention is operated in the turbulent regime, the gaseous reaction mixture is present as small bubbles whose existence is extremely short. The bubbles travel only a few feet as they constantly break-up, coalesce and reform. Therefore when practicing the present conversion process it is unnecessary to provide baffles in the reactor vessel as is often found necessary to control the large bubbles encountered in bubbling fluidized beds, such as those employed in the prior art processes.

In order to assure that the practice of the present invention occurs in the turbulent regime, several criteria concerning solid catalyst physical properties, reactor configuration and superficial fluid velocity must be satisfied simultaneously.

Table 1 below sets forth useful parameters required to achieve fluidization in the turbulent regime in accordance with the process of the present invention. When employing a ZSM-5 type zeolite catalyst in fine powder form such a catalyst would comprise the zeolite impregnated on a suitable support with a solid density (weight of a representative individual particle divided by its apparent "outside" volume) in the range from 0.6–2 g/cc, preferably 0.9–1.6 g/cc. The catalyst particles can be in a wide range of particle sizes, 0–250 μm, with an average particle size of between 30 and 100 μm, preferably in the range of 0–150 μm and with the average particle size between 40 and 80 μm. When these solid particles are placed in a fluidized bed where the superficial fluid velocity is 0.5–7 fps, preferably 0.8–3 fps, operation in the turbulent regime is obtained. The velocity specified here is for an operation at a low reactor pressure of say less than 60 psia. Those skilled in the art will appreciate that at higher pressures, a lower gas velocity may be employed to ensure operation in the turbulent fluidization regime.

The reactor can assume any commercially plausible configuration but two important criteria should be satisfied: the bed of catalyst in the reactor should be more than 8 feet in height, preferably more than 15 feet while the diameter of the reactor should normally be large for a commercial operation, say 8–40 feet I.D. If operation in a much smaller diameter reactor is contemplated, the superficial fluid velocity and the minimum bed height would have to be raised to insure operation in the turbulent fluidization regime. These parameters will vary with the specific system in question

TABLE I

| Criterion | Proposed Range | Preferred Range |
|---|---|---|
| Catalyst particle density* | 0.6–2 g/cc | 0.9–1.6 g/cc |
| Catalyst particle size range | 0–250 μm | 0–150 μm |
| Avg catalyst particle size | 30–100 μm | 40–80 μm |
| Percent Catalyst fines (<40 μm) | 5–40% | 15–30% |
| Superficial fluid velocity | 0.5–7 ft/s | 0.8–3 ft/s |
| Pressure | 15–100 psia | 25–50 psia |
| Catalyst bed height | >8 ft | >15 ft |
| Reactor diameter (for large scale operation) | 8–40 ft | depends on desired throughput |

*density = $\frac{\text{weight of one representative particle}}{\text{its apparent volume}}$ but can be determined quite readily without undue experimentation by those skilled in the fluidized art. Removal of heat of reaction can be accomplished by the various options disclosed in the prior art.

Operation in the turbulent fluidization regime is also possible for a completely different set of conditions, for example, with much larger catalyst particles. For particle sizes of 200–800 μm (Group B powders), which are generally less desirable than those discussed above, the other criteria will have to be varied. For example, a much higher gas velocity of say 10–20 fps should be employed. Those skilled in the art can appreciate that the other parameters will have to be adjusted likewise to assure fluidization in the turbulent regime. Again, these operating conditions can be determined by the skilled artisan without an undue amount of experimentation.

Operation in the turbulent fluidization regime insures a random, more homogenous condition for the fluid bed. Bubbles are small, short lived and in a constant state of agitation, break-up and coalescence thereby providing good contact between the gaseous reactants and the catalyst particles. These bubbles do not travel more than several feet in any direction in the reactor, thus minimizing gas by-passing and heterogeneity of the reactor.

Operation of the conversion process of this invention in the turbulent fluidization regime provides a far more desirable operation than in the bubbling fluidization regime where large bubbles cause a deterioration in reactor performance.

The temperature in the fluid catalyst bed of this invention is substantially uniform. Fluid bed temperatures may range from about 575° to about 800° F. Usually, bed temperatures of about 650° to about 800° F are employed for producing gasoline while bed temperatures of about 575° to about 700° F. are used when a highly olefinic product is desired.

In a methanol conversion and operating environment, it is contemplated achieving a methanol conversion of greater than 95% and preferably about 99.5% to minimize the loss of difficult to recover methanol in process formed water. When it is desired to change product selectivity to one of high olefin content as opposed to high aromatics yield, the reaction time as a function of space velocity may be reduced by increasing the space velocity. On the other hand, aromatic formation is enhanced by a reduction in reactant space velocity to increase time of contact between methanol reactant product and catalyst. A good balance in product selectivity between olefins, aromatics and paraffins may be had by a proper selection of reaction conditions.

What is claimed is:

1. A process for converting methanol, dimethylether or mixtures thereof to a gasoline-rich product containing at least about 70% of a hydrocarbon product higher boiling than the reactant comprising the steps of passing the reactant upwardly in a catalytic reactor through a fluidized bed of catalyst particles comprising ZSM-5 crystalline zeolite under conditions effective to provide turbulent regime fluidization, said catalyst particles having a particle density of about 0.9 to about 1.6 g/cc, an average catalyst particle size of about 40 to about 80 μm including about 5 to 40 weight percent of catalyst fines having a particle size less than 40 μm; and wherein effective conditions include a superficial fluid velocity of about 0.5 to about 7 fps, a pressure of about 15 to about 100 psia and a catalyst bed height of more than 8 feet, thereby converting more than 95 percent of the reactant in the reactor.

2. A fluidized bed catalytic process for at least 95 percent conversion of methanol to hydrocarbons comprising maintaining a fluidized bed of ZSM-5 type catalyst particles in a turbulent reactor bed, said catalyst having a particle density of about 0.9 to 1.6 g/cm$^3$ and a size range up to about 150 μm, and average catalyst particle size of about 40 to 80 μm containing abot 15 to 30 weight percent of fine particles having a particle size less than 40 μm;

passing hot methanol vapor upwardly through the fluidized catalyst bed under turbulent flow conditions; and maintaining turbulent fluidized bed conditions through the reactor bed between transition velocity and transport velocity at a superficial fluid velocity of about 0.8 to 3 feet per second.

3. A fluidized bed process according to claim 2 wherein the fluidized bed density is about 200 to 355 kg/m$^3$, measured at the bottom of the bed.

* * * * *